US 6,558,618 B1

(12) United States Patent
Dent, Jr.

(10) Patent No.: US 6,558,618 B1
(45) Date of Patent: May 6, 2003

(54) ANTI-INFECTION FORMULATION AND DELIVERY METHOD

(76) Inventor: James L Dent, Jr., R.R. 1 Box 191A, Lincoln Hwy., Thomasville, PA (US) 17364

( * ) Notice: Subject to any disclaimer, the term of this patent is extended or adjusted under 35 U.S.C. 154(b) by 0 days.

(21) Appl. No.: 09/300,613

(22) Filed: Apr. 27, 1999

(51) Int. Cl.[7] ............................................... A61L 9/015
(52) U.S. Cl. ........................... 422/4; 424/114; 424/400; 514/849; 514/855; 514/957; 514/958; 514/959; 128/203.26
(58) Field of Search ................................ 422/4, 5, 125, 422/305, 306, 123, 124; 424/76.2, 76.8, 114, 400; 514/957, 958, 959, 39, 9, 10, 11, 692, 826, 849, 851, 855, 888; 128/200.24, 203.12, 203.26

(56) References Cited

U.S. PATENT DOCUMENTS 2,676,134 A * 4/1954 Felsenfeld
2,822,314 A * 2/1958 Ferlauto et al.
5,322,689 A * 6/1994 Hughes et al.
5,897,009 A * 4/1999 O'Meara ..................... 215/48

FOREIGN PATENT DOCUMENTS

WO    WO-98/52540 A1 * 11/1998

OTHER PUBLICATIONS

Physicians' Desk Reference entry for Neosporin® + Pain Relief Maximum Strength, prior art.*
Physicians' Desk Reference entry for Vicks® Vaposteam® , prior art.*

* cited by examiner

Primary Examiner—Elizabeth McKane
(74) Attorney, Agent, or Firm—Michael I. Kroll

(57) ABSTRACT

A method of dispersing, in water vapor, an anti-infective therapeutic composition (10) into the air in a room (36), in order to treat or prevent transmission of upper respiratory infections, includes: adding to a reservoir of liquid water in a vaporizer (34), a therapeutic composition (10) containing one or more antibiotics (14), alcohol (16), an analgesic (18) and an expectorant (20); and vaporizing the therapeutic composition (10) into the air along with the water in the vaporizer reservoir for inhalation by persons in the room.

7 Claims, 4 Drawing Sheets

ANTI-INFECTION FORMULATION AND DELIVERY METHOD

BACKGROUND OF THE INVENTION

Field of the Invention

Figure 1:
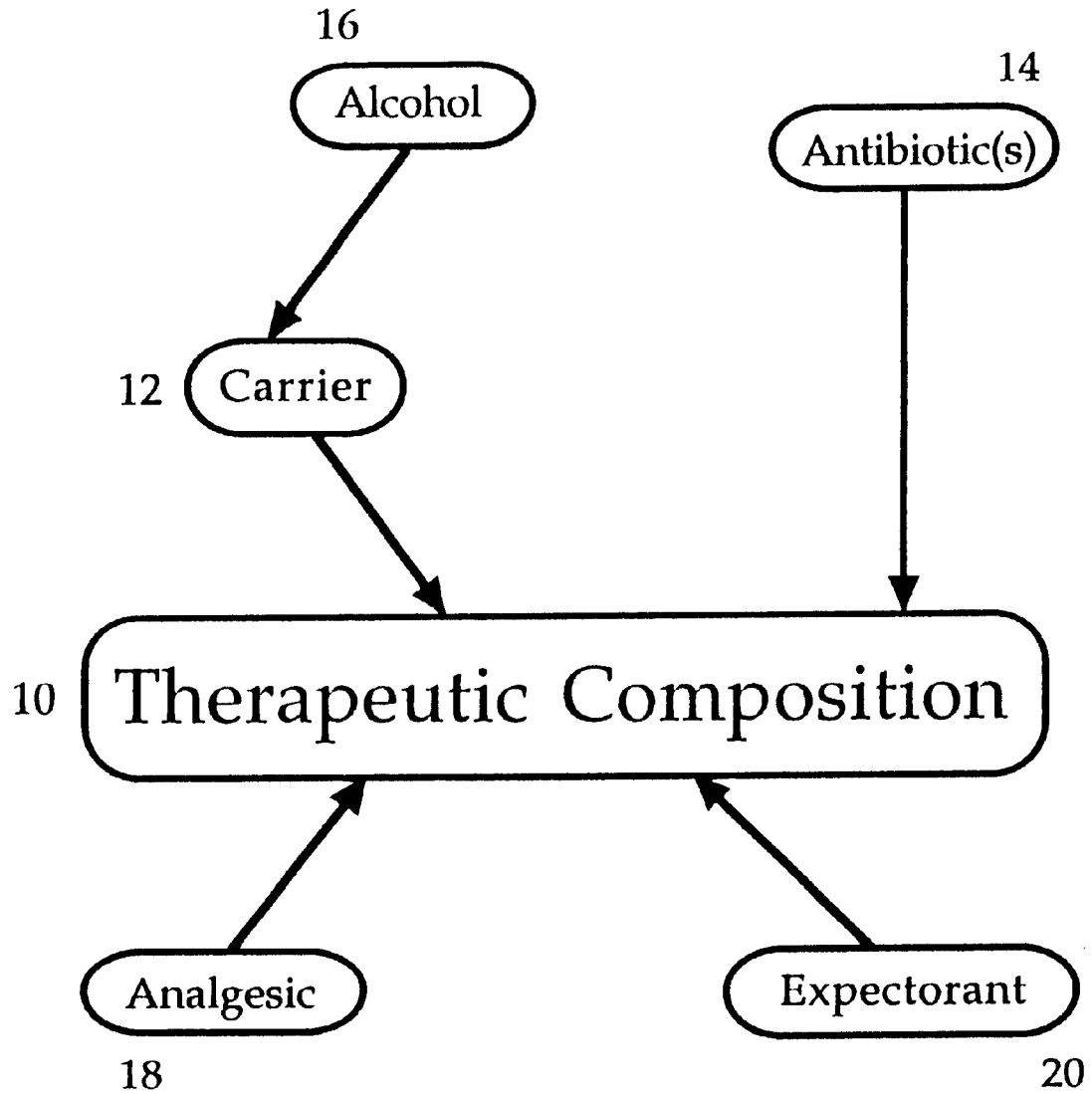
Figure 2:
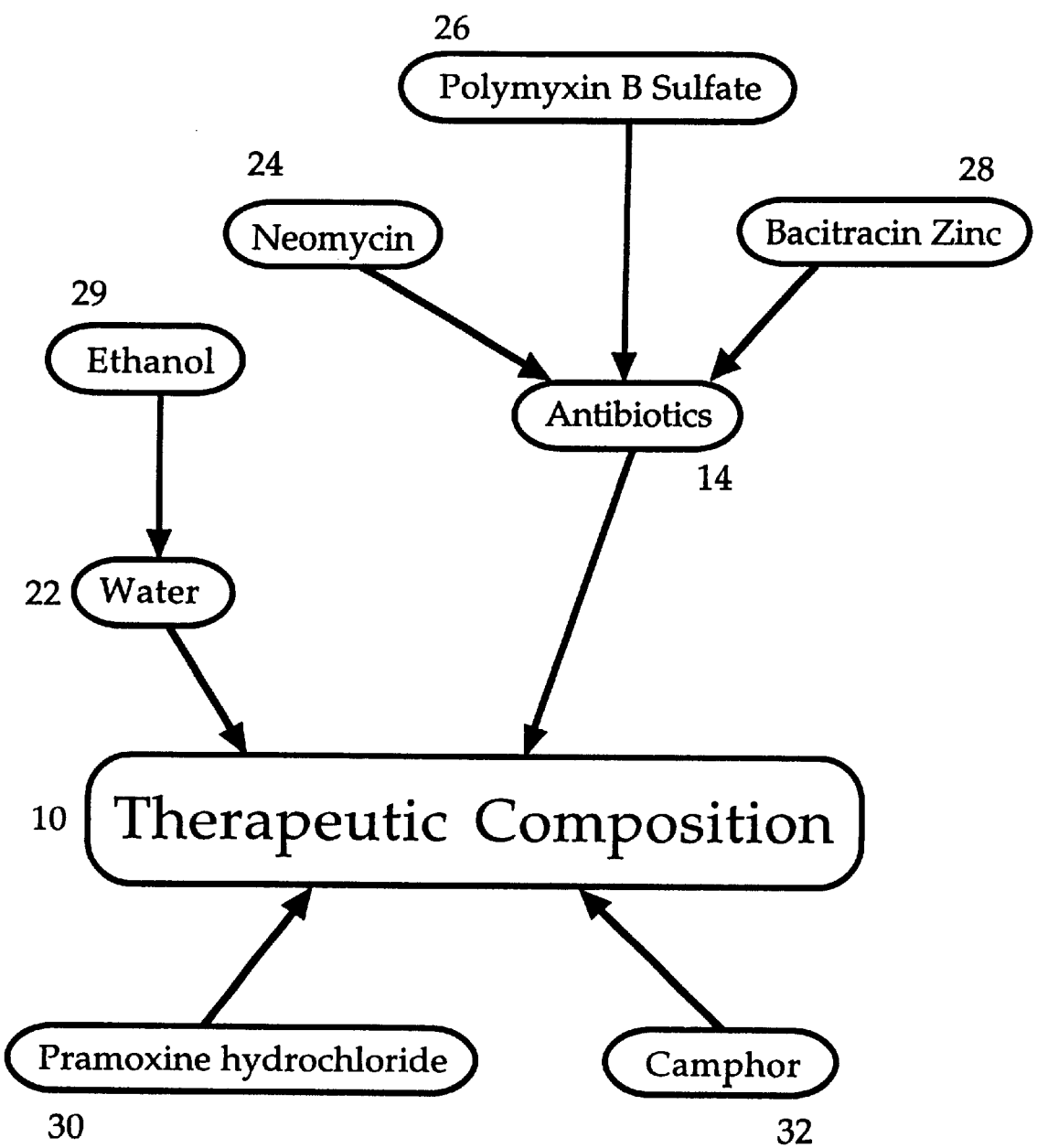
Figure 3:
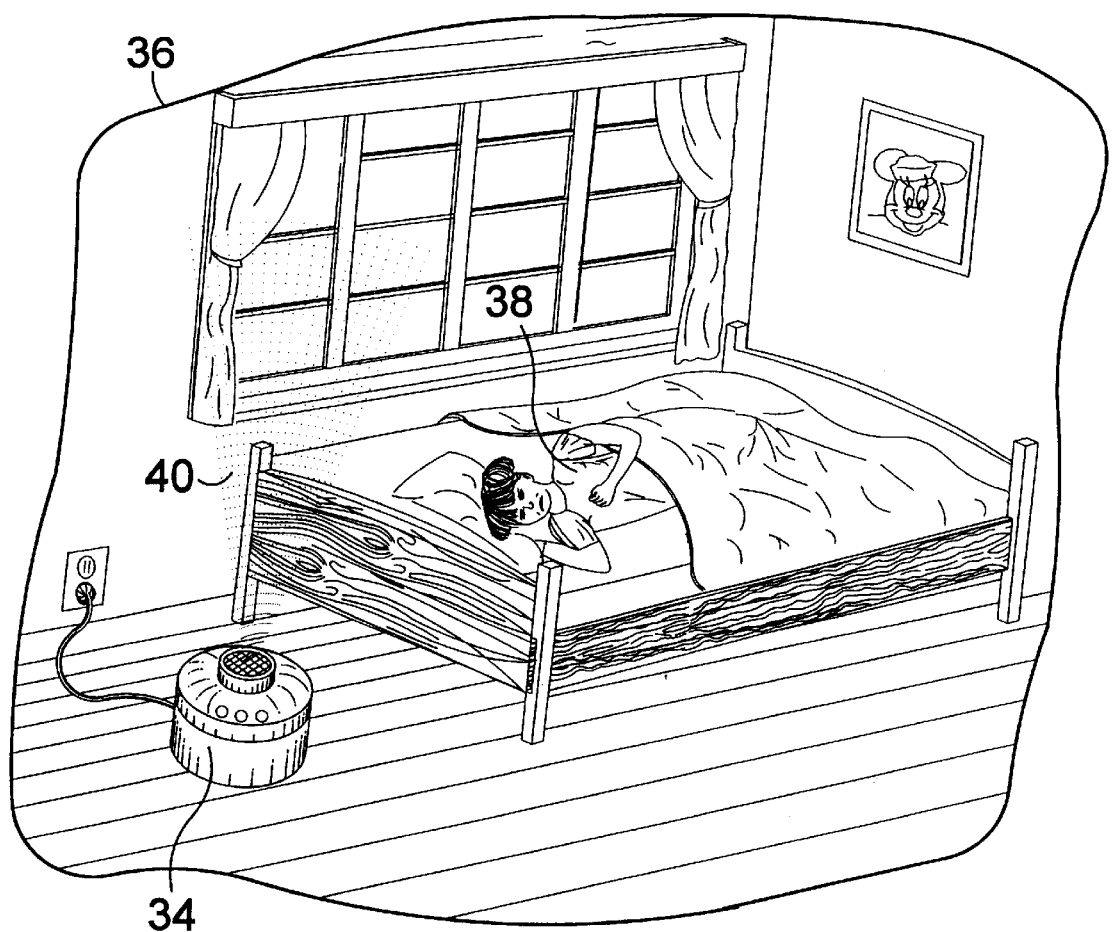
Figure 4:
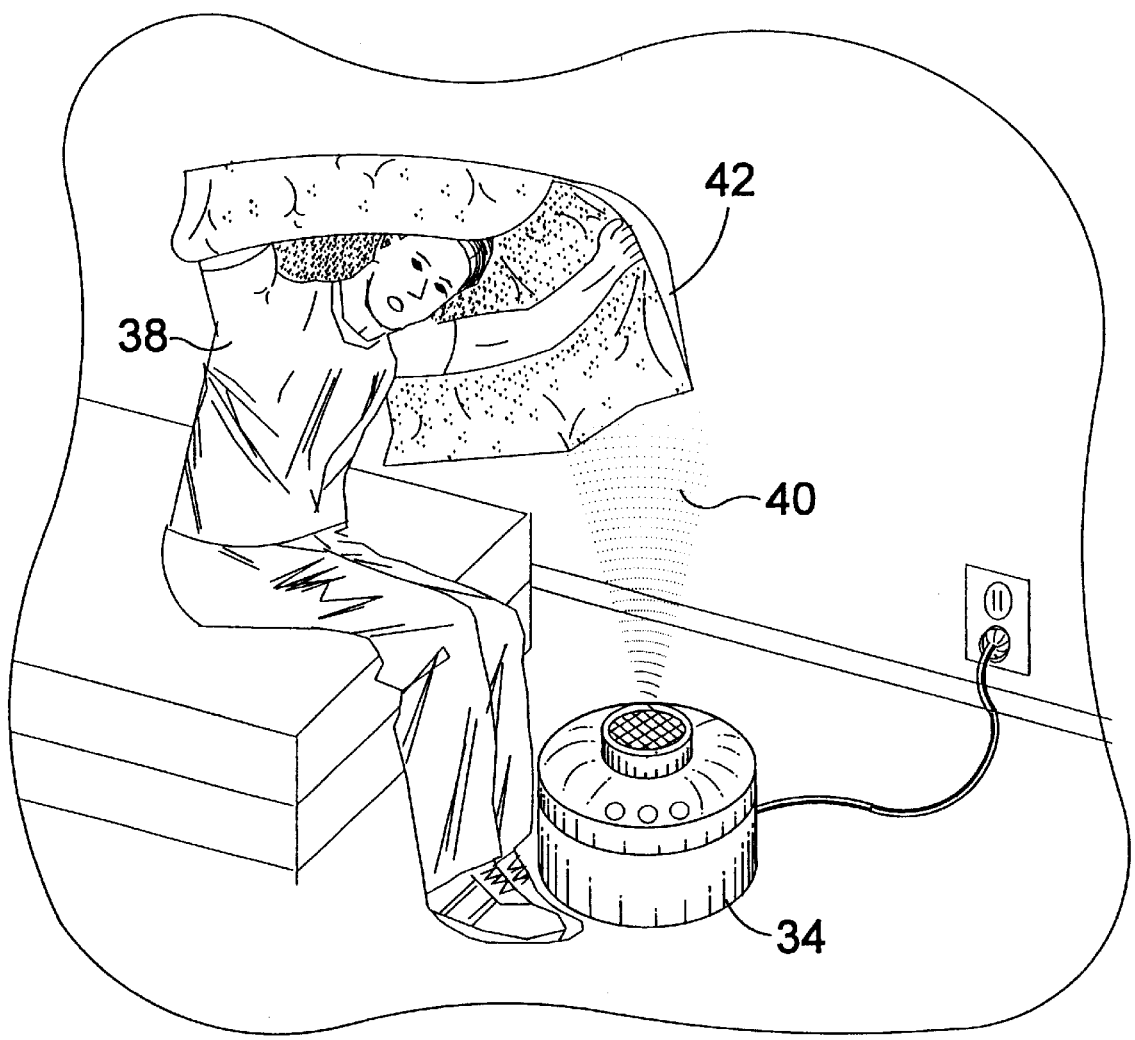

The instant invention relates generally to compositions for alleviating the symptoms of upper respiratory infections in humans and more specifically to anti-infection formulations for vaporizing into the air for delivery via inhalation.

SUMMARY OF THE INVENTION

The present invention is concerned with an anti-infection composition for alleviating the symptoms of upper respiratory infections in humans and more specifically to anti-infection formulations for vaporizing into the, air for delivery to a person in need of such treatment via inhalation.

A primary object of the present invention is to provide a therapeutic composition for addition to the water of a vaporizer for inhalation by a person in need of treating or preventing transmission of an upper respiratory tract infection (URTI).

Another object of the present invention is to provide a therapeutic composition for addition to the water of a vaporizer which contains one or more antibiotics, an analgesic and an expectorant.

A further object of the present invention is to provide a therapeutic composition for addition to the water of a vaporizer which contains camphor.

Yet another object of the present invention is to provide a method of treating the air of a room with a therapeutic composition which is added to the water of a vaporizer.

Another object of the present invention is to provide a therapeutic composition and method of use which is simple and easy to use by the home user.

A further object of the present invention is to provide a therapeutic composition and method of use which is inexpensive to produce and easy to dispose.

The foregoing and other objects, advantages and characterizing features will become apparent from the following description of certain illustrative embodiments of the invention.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings. Attention is called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

FIG. 1 is a diagrammatic view of various components which may find use in the present invention.

FIG. 2 is a diagrammatic view similar to that of FIG. 1, showing the preferred components.

FIG. 3 is a graphic depiction of the present invention being utilized in the room of a person.

FIG. 4 is a graphic depiction of further method of using the invention.

DESCRIPTION OF THE PREFERRED EMBODIMENTS

Turning now descriptively to the drawings, in which similar reference characters denote similar elements throughout the several views, the figures illustrate a therapeutic composition and method of use of the present invention. With regard to the reference numerals used, the following numbering is used throughout the various drawing figures.

10 therapeutic composition of the present invention
12 carrier for 10
14 antibiotic component of 10
16 alcohol component of 10
18 analgesic component of 10
20 expectorant component of 10
22 water
24 neomycin
26 polymyxin B sulfate
28 bacitracin zinc
29 ethanol
30 pramoxine hydrochloride
32 camphor
34 vaporizer
36 room
38 person in need of treatment
40 vapor from 34

FIG. 1 through FIG. 4 illustrate a therapeutic composition 10 which is to be added to the water of a vaporizer 34 in order to disperse the therapeutic composition, in admixture with water vapor 40 into the air in a room 36 so that it may be inhaled by a person 38 in need of treating or preventing an upper respiratory tract infection.

It is well known in the art to treat the air inhaled by a person infected with an URTI with water vapor. Most commonly, a small, room-sized vaporizer 34 is utilized which is sufficient to humidify a single room 36. In this case, the vaporizer 34 generally contains a reservoir for holding a quantity of water, typically about 2 to 6 liters in volume, which is mechanically vaporized into the air of the room of the person 38 being treated. The present invention provides for a therapeutic composition 10 which is added to the water in the reservoir of the vaporizer 34 so that the therapeutic composition 10 can be vaporized 40, along with the water in the reservoir, into the air of the room so as to be directly inhaled by the person 38 in need of treatment. Speaking generally, the therapeutic composition 10, as illustrated in FIG. 1, includes one or more antibiotics 14, alcohol 16, an analgesic 18 and an expectorant 20, all in a suitable alcohol 16 containing carrier 12.

With regard to the antibiotics 14, it is preferred that the composition 10 contain three or more different antibiotics in combination. A preferred combination is a mixture of polymyxin B sulfate 26, bacitracin zinc 28 and neomycin 24. When utilized in a single room sized vaporizer 34, a preferred proportion for the three antibiotics is about 50,000 units polymyxin B sulfate 26, about 2,500 units bacitracin zinc 28 and about 18 mg neomycin 24. It is anticipated that a suitable range for these antibiotics would be from about 20,000 to about 100,000 units polymyxin B sulfate 26, from about 1500 to about 5,000 units bacitracin zinc 28, and from about 10 to about 40 mg neomycin 24. It can readily be appreciated, however, that larger or smaller capacity vaporizers may require proportionally more or less of the combination, with the proportions of each remaining the same.

Also included in the composition is an analgesic 18, for providing relief of aches and pains associated with colds, flu, and other URTIs. For purposes of the present invention, a preferred analgesic 18 is pramoxine hydrochloride 30. A suitable dosage level is from about 30 to about 100 mg, most preferably about 50 mg pramoxine hydrochloride 30. As discussed above with regard to the antibiotics 14, a larger or smaller capacity vaporizer 34 would require proportionally more or less analgesic 18.

The composition of the present invention also contains, as an active component, an expectorant 20. The preferred expectorant is camphor 32. A suitable dosage level is from about 500 to about 2,000 mg, most preferably about 900 mg camphor 32. Again, a larger or smaller capacity vaporizer 34 would require proportionally more or less expectorant 20.

With regard to the carrier 12, it is necessary to include an alcohol 16 in order to dissolve the camphor 32, which is insoluble in water 22. The addition of an alcohol 16 also promotes the production of steam, due to the low boiling point of alcohol as compared with water. The preferred alcohols are low molecular weight alkyl alcohols such as methanol, ethanol 29, propanol, isopropanol and the like. The preferred alcohol 16 is ethanol 29. The carrier 12 can, and preferably does, contain water 22. The proportions of alcohol and water can vary widely, as most proportions will be suitable for practicing the invention, but a preferred range of proportions of water to ethanol is from about 1:10 to about 5:1, respectively by weight, with a particularly preferred proportion being about 1 part water to 5 parts ethanol, on a weight to weight basis.

When added to the vaporizer 34, the therapeutic composition 10 of the present invention should constitute a volume significantly less than the volume of the water in the vaporizer. The active constituents (the antibiotics 14, analgesic 18 and expectorant 20) of the composition 10 do not generally contribute significant volume to the composition. Accordingly, the volume of the carrier liquid 12 approximates the total volume of the entire therapeutic composition 10. A convenient and preferred volume of carrier liquid 12 is from about 5 to about 30 ml, most preferably about 15 ml, roughly equivalent to one tablespoon, or one-half of a fluid ounce.

It will be understood that each of the elements described above, or two or more together, may also find a useful application in other types of applications differing from the type described above. These include, for example, conditions other than URTIs which may be suitably treated via pulmonary administration of antibiotics.

While the invention has been illustrated and described as embodied in a therapeutic composition and method of use, it is not intended to be limited to the details shown, since it will be understood that various omissions, modifications, substitutions and changes in the forms and details of the formulation illustrated and in its operation can be made by those skilled in the art without departing in any way from the spirit and scope of the present invention. For example, any suitable antibiotic or group of antibiotics may be used instead of the neomycin, polymyxin B sulfate and bacitracin zinc combination described. Also, the analgesic may be selected from the many analgesics available today rather than the pramoxine hydrochloride described. And although camphor has been described as the preferred expectorant, it should be appreciated that other expectorants, both pharmaceutical and natural, may be similarly employed. Furthermore, as the alcohol serves primarily to aid in solubilizing the water insoluble components in addition to promoting steam production, it should be readily appreciated that other short chain alcohols, such as methanol, propanol, isopropanol, et al., may also be employed.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed as new and desired to be protected by Letters Patent is set forth in the appended claims.

I claim:

1. A method of treating the air in a room with water vapor, comprising:

a) adding to a reservoir of liquid water in a vaporizer, a therapeutic composition dissolved in a liquid carrier of alcohol containing:

i) the combination of at least three antibiotics comprising from about 20,000 to about 100,000 units of polymyxin B sulfate, from about 1500 to about 5000 units of bacitracin zinc, and from about 10 to about 40 mg neomycin;

ii) an analgesic comprising pramoxine hydrochloride in the amount of from about 30 to about 100 mg; and iii) an expectorant comprising camphor in the amount of from about 500 to 2,000 mg; and b) vaporizing said therapeutic composition into the air along with the water in the vaporizer reservoir.

2. The method of claim 1, wherein said alcohol is ethanol in the amount of from about 3 to about 25 g.

3. The method of claim 2, wherein said three antibiotics comprise a combination of about 50,000 units polymyxin B sulfate, about 2,500 units bacitracin zinc, and about 18 mg neomycin.

4. The method of claim 3, wherein said analgesic comprises about 50 mg pramoxine hydrochloride.

5. The method of claim 4, wherein said expectorant comprises about 900 mg camphor.

6. The method of claim 5, wherein said alcohol comprises about 11 g ethanol.

7. The method of claim 6, wherein said therapeutic composition further comprises about 2.2 g water.

\* \* \* \* \*